(12) United States Patent
Black et al.

(10) Patent No.: US 11,896,826 B1
(45) Date of Patent: Feb. 13, 2024

(54) SYSTEMS, DEVICES AND METHODS FOR CALORIC VESTIBULAR STIMULATION

(71) Applicant: Scion Neurostim, Inc., Durham, NC (US)

(72) Inventors: Robert D. Black, Chapel Hill, NC (US); Duncan Bathe, Fitchburg, WI (US)

(73) Assignee: SCION NEUROSTIM, INC., Durham, NC (US)

(*) Notice: Subject to any disclaimer, the term of this patent is extended or adjusted under 35 U.S.C. 154(b) by 0 days.

(21) Appl. No.: 18/068,069

(22) Filed: Dec. 19, 2022

(51) Int. Cl.
*A61N 1/36* (2006.01)
*A61F 7/00* (2006.01)

(52) U.S. Cl.
CPC .. *A61N 1/36039* (2017.08); *A61F 2007/0005* (2013.01)

(58) Field of Classification Search
CPC ........................................................ A61F 11/12
See application file for complete search history.

(56) References Cited

U.S. PATENT DOCUMENTS

| | | | |
|---|---|---|---|
| 6,300,150 B1 | 10/2001 | Venkatasubramanian | |
| 9,526,653 B2 | 12/2016 | Rogers et al. | |
| 9,532,900 B2 | 1/2017 | Smith et al. | |
| 10,617,333 B2* | 4/2020 | Brown | H04R 1/406 |
| 2006/0086118 A1 | 4/2006 | Venkatasubramanian et al. | |
| 2007/0028956 A1 | 2/2007 | Venkatasubramanian et al. | |
| 2007/0269072 A1* | 11/2007 | Pfanner | A61F 11/12 |
| | | | 381/379 |
| 2016/0199228 A1* | 7/2016 | Haukap | A61F 11/14 |
| | | | 2/209 |

OTHER PUBLICATIONS

Teggi, et al., "Migrainous Vertigo: Results of Caloric Testing and Stabilometric Findings", Headache: The Journal of Head and Face Pain, 49(3), 2009, 435-444.

Zhang, et al., "Change of extracellular ascorbic acid in the brain cortex following ice water vestibular stimulation: an on-line electrochemical detection coupled within vivomicrodialysis sampling for guinea pigs", Chinese Medical Journal, 121(12), 2008, 1120-1125.

* cited by examiner

*Primary Examiner* — Kaitlyn E Smith
(74) *Attorney, Agent, or Firm* — Myers Bigel, P.A.

(57) ABSTRACT

An in-ear stimulation device for administering caloric stimulation to the ear canal of a subject includes a frame defining a perimeter and having a center region, at least one tensioning member in the center region of the frame and being held by the frame, and an earpiece connected to the tensioning member in the center region of the frame. The frame is configured to generally rest on a head and around an ear of the subject such that the earpiece is positioned in the ear canal of the subject and the tensioning member exerts a force on the earpiece toward the ear canal of the subject.

22 Claims, 9 Drawing Sheets

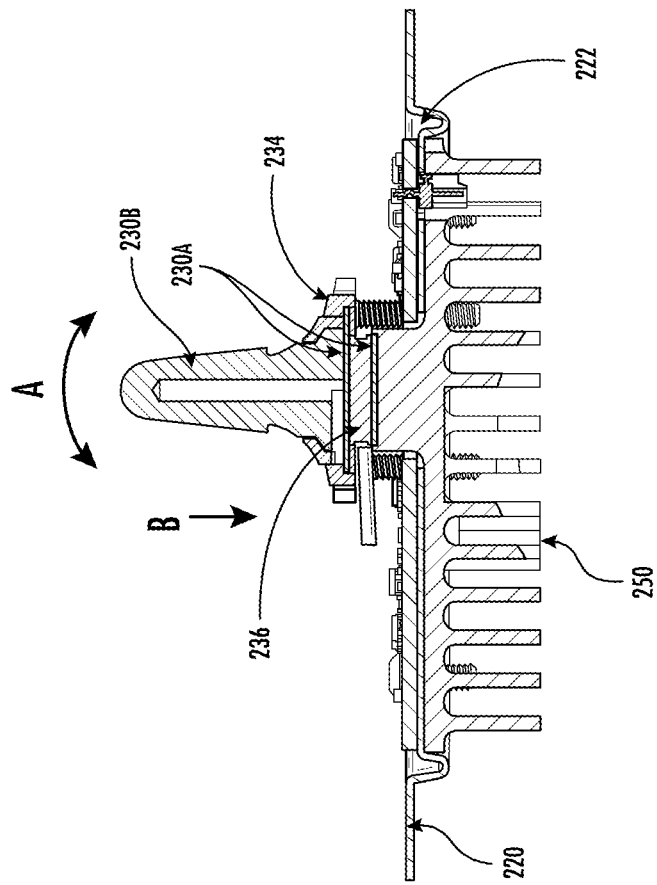
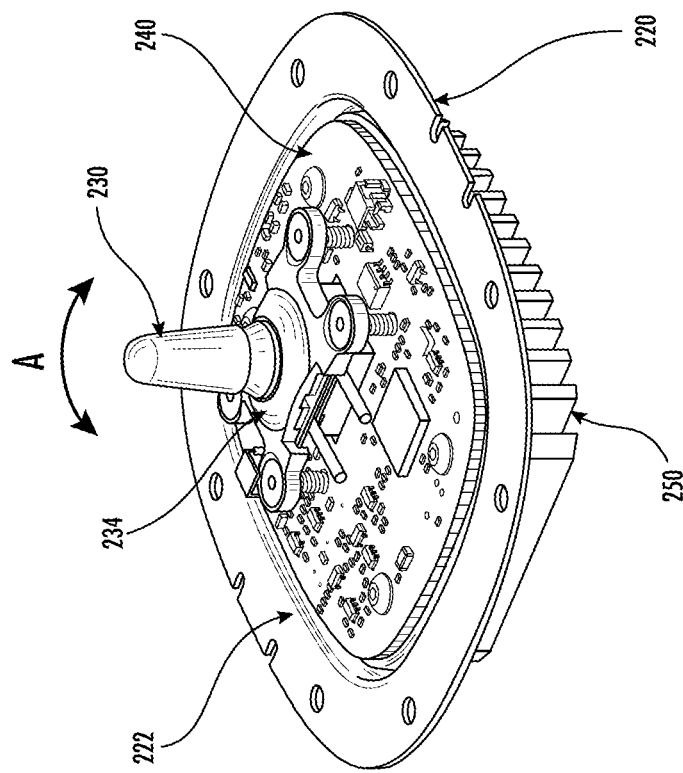
FIG. 6A
FIG. 6B

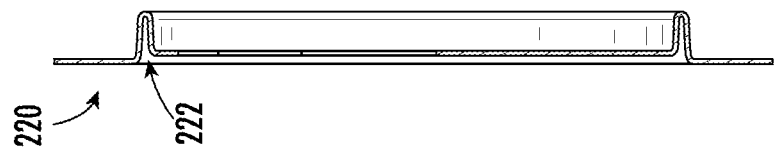
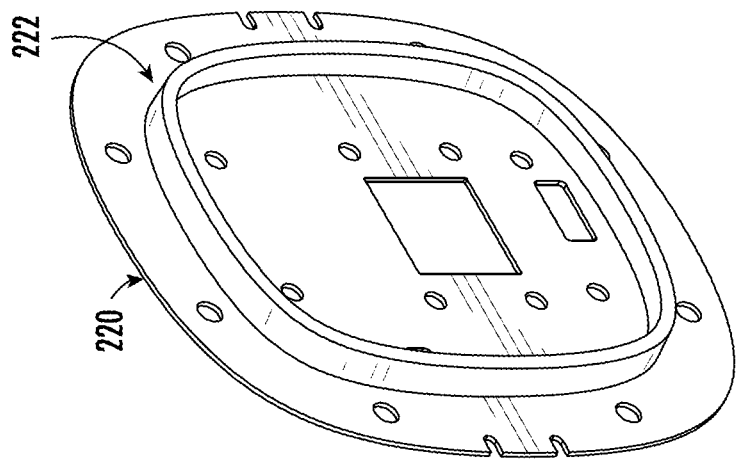
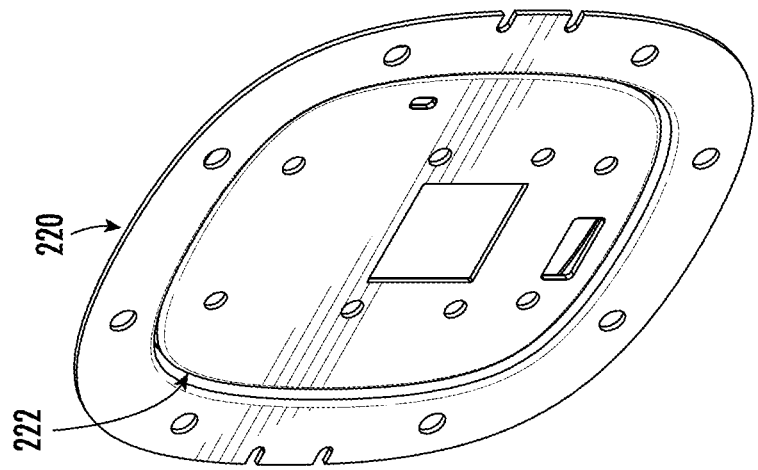

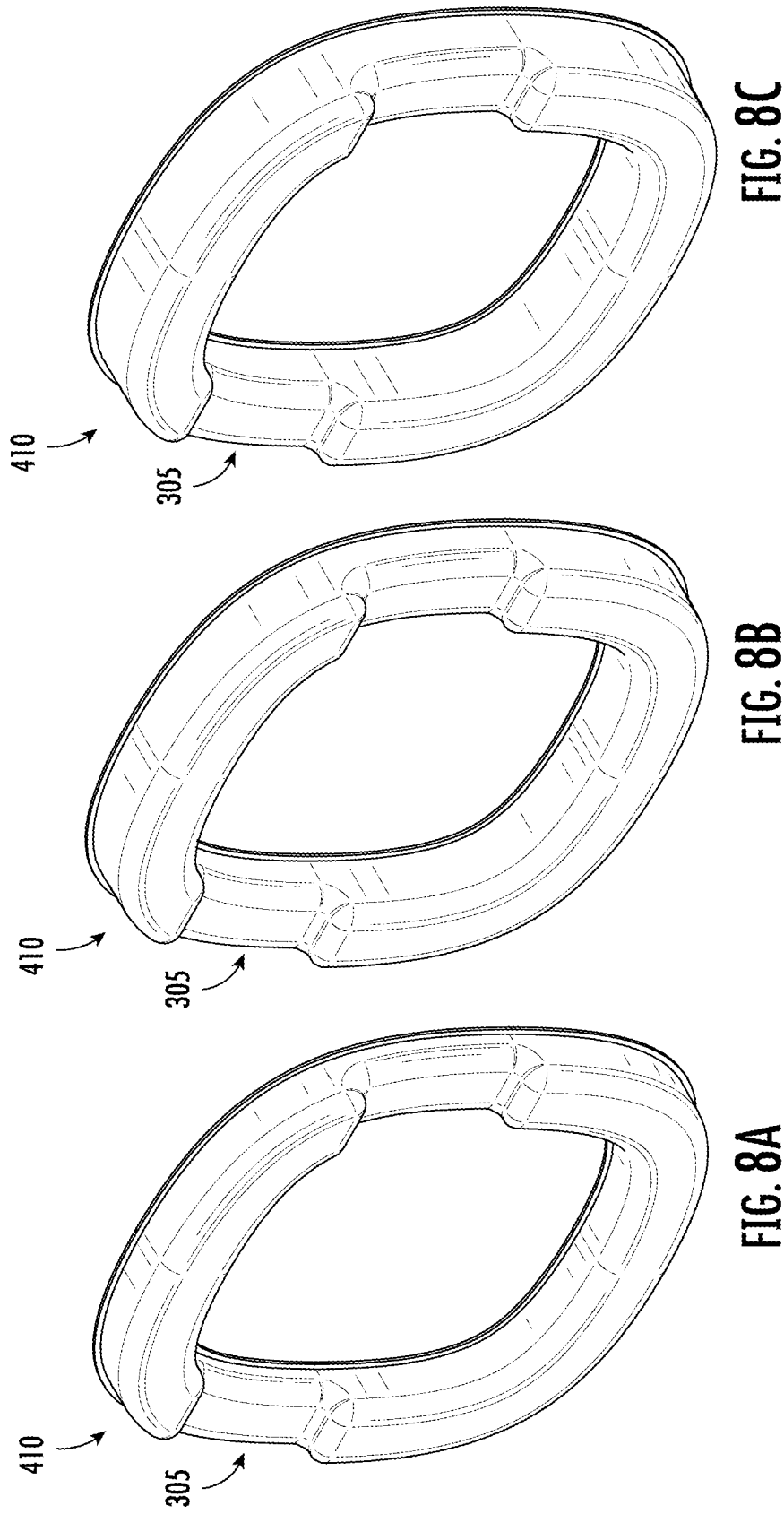

SYSTEMS, DEVICES AND METHODS FOR CALORIC VESTIBULAR STIMULATION

FIELD OF THE INVENTION

The present invention relates to caloric vestibular stimulation, and in particular, to caloric vestibular stimulation earpieces with increased comfort features for the user.

BACKGROUND

Caloric vestibular stimulation ("CVS") has long been known as a diagnostic procedure for testing the function of the vestibular system. In the traditional hospital setting, water-based caloric tests are used to study the function of the two vestibular labyrinths (often to diagnose balance disorders) and to assess levels of consciousness after acute or chronic brain injury.

More recently, time-varying CVS (tvCVS) has been used for delivering therapeutic stimulation to the nervous system, the vestibular sensory network, of an individual with the aim of treating a variety of medical conditions. A solid-state delivery system, versus water or air-based irrigations used in the diagnostic procedure, has been demonstrated in both the home and hospital settings. However, improvements in patient comfort relating to the tvCVS delivery device may be desired for enhanced treatment acceptance and compliance.

SUMMARY OF EMBODIMENTS OF THE INVENTION

In some embodiments, an in-ear stimulation device for administering caloric stimulation to the ear canal of a subject includes a frame defining a perimeter and having a center region, at least one tensioning member in the center region of the frame and being held by the frame, and an earpiece connected to the tensioning member in the center region of the frame. The frame is configured to generally rest on a head and around an ear of the subject such that the earpiece is positioned in the ear canal of the subject and the tensioning member decouples or reduces the force on the earpiece (in the ear canal) exerted by the frame from the minimal force needed for the earpiece to achieve a good fit and comfort. Accordingly, the force on the earpiece is reduced for user comfort but is sufficient to provide a close fit for thermal contact. In some embodiments, increased user comfort may increase user compliance with treatment.

BRIEF DESCRIPTION OF THE DRAWINGS

The accompanying drawings, which are incorporated in and constitute a part of the specification, illustrate embodiments of the invention and, together with the description, serve to explain principles of the invention.

FIGS. 6A-6B are a perspective view (FIG. 6A) and a side cross sectional view (FIG. 6B) of a portion of the in-ear stimulation device of FIG. 5.

FIGS. 7A-7C are a front perspective view (FIG. 7A), a bottom perspective view (FIG. 7B), and a cross sectional view of the tensioning member of FIGS. 3-4.

FIGS. 8A-8C are perspective views of a small cushioning member (FIG. 8A), a medium cushioning member (FIG. 8B), and a large cushioning member (FIG. 8C).

DETAILED DESCRIPTION OF EMBODIMENTS OF THE INVENTION

Figure 1:
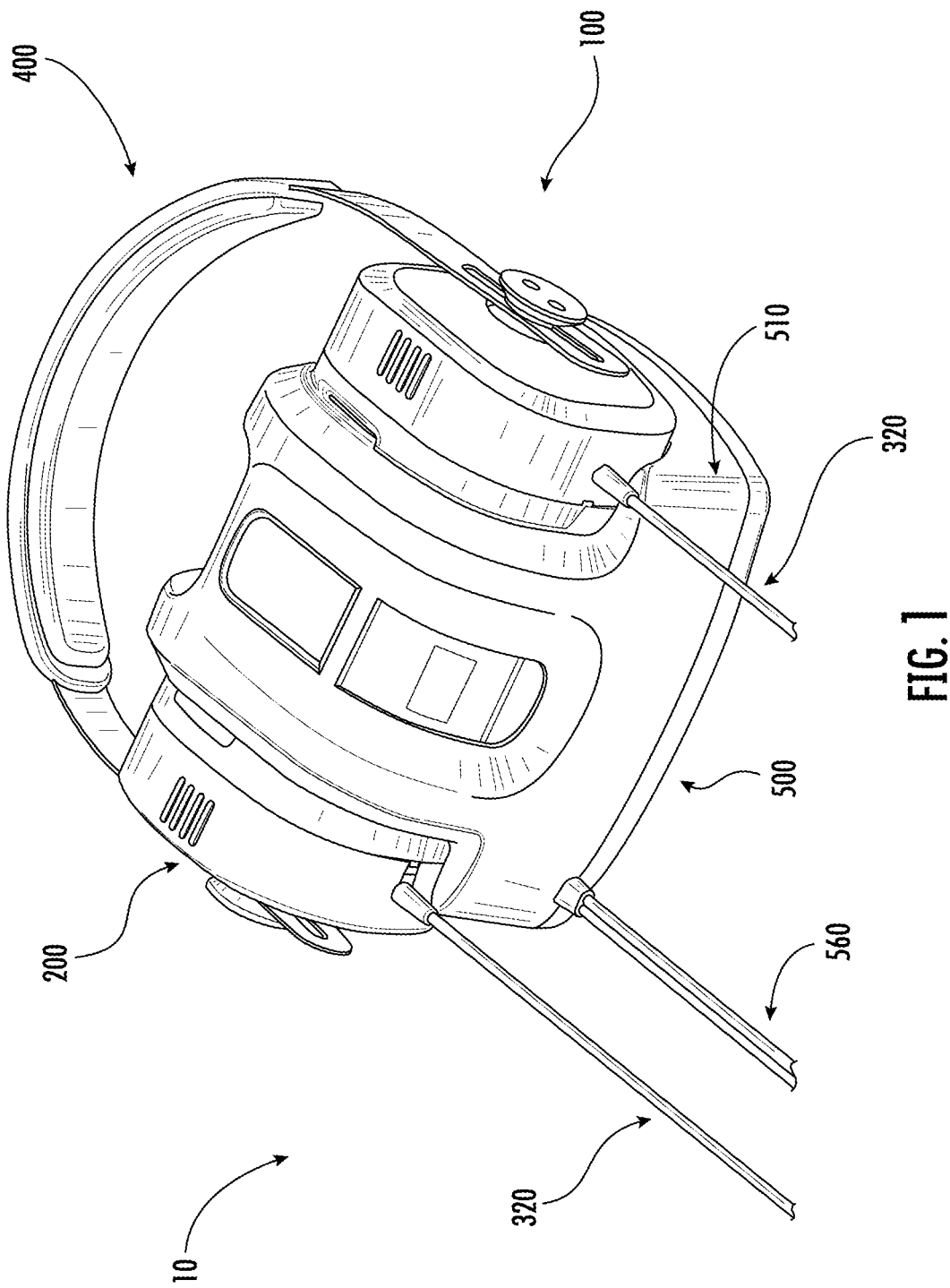
FIG. 1 is perspective view of an in-ear tvCVS stimulation system having headset and controller base according to some embodiments of the present invention.

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

Definitions

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

The present invention is described below with reference to block diagrams and/or flowchart illustrations of methods, apparatus (systems) and/or computer program products according to embodiments of the invention. It is understood that each block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the function/act specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, the present invention may be embodied in hardware and/or in software (including firmware, resident software, micro-code, etc.). Furthermore, embodiments of the present invention may take the form of a computer program product on a computer-usable or computer-readable non-transient storage medium having computer-usable or computer-readable program code embodied in the medium for use by or in connection with an instruction execution system.

The computer-usable or computer-readable medium may be, for example but not limited to, an electronic, optical, electromagnetic, infrared, or semiconductor system, apparatus, or device. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory such as an SD card), an optical fiber, and a portable compact disc read-only memory (CD-ROM).

As used herein, the term "vestibular system" has the meaning ascribed to it in the medical arts and includes but is not limited to those portions of the inner ear known as the vestibular apparatus and the vestibulocochlear nerve. The vestibular system, therefore, further includes, but is not limited to, those parts of the brain that process signals from the vestibulocochlear nerve.

"Treatment," "treat," and "treating" refer to reversing, alleviating, reducing the severity of, delaying the onset of, inhibiting the progress of, or preventing a disease or disorder as described herein, or at least one symptom of a disease or disorder as described herein (e.g., treating one or more of tremors, bradykinesia, rigidity or postural instability associated with Parkinson's disease; treating one or more of intrusive symptoms (e.g., dissociative states, flashbacks, intrusive emotions, intrusive memories, nightmares, and night terrors), avoidant symptoms (e.g., avoiding emotions, avoiding relationships, avoiding responsibility for others, avoiding situations reminiscent of the traumatic event), hyperarousal symptoms (e.g., exaggerated startle reaction, explosive outbursts, extreme vigilance, irritability, panic symptoms, sleep disturbance) associated with post-traumatic stress disorder). In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved—for example, to prevent or delay their recurrence. Treatment may comprise providing neuroprotection, enhancing cognition and/or increasing cognitive reserve. Treatment may be as an adjuvant treatment as further described herein.

"Adjuvant treatment" as described herein refers to a treatment session in which the delivery of one or more thermal waveforms to the vestibular system and/or the nervous system of a patient modifies the effect(s) of one or more active agents and/or therapies. For example, the delivery of one or more thermal waveforms to the vestibular system and/or the nervous system of a patient may enhance the effectiveness of a pharmaceutical agent (by restoring the therapeutic efficacy of a drug to which the patient had previously become habituated, for example). Likewise, the delivery of one or more thermal waveforms to the vestibular system and/or the nervous system of a patient may enhance the effectiveness of counseling or psychotherapy. In some embodiments, delivery of one or more thermal waveforms to the vestibular system and/or the nervous system of a patient may reduce or eliminate the need for one or more active agents and/or therapies. Adjuvant treatments may be effectuated by delivering one or more thermal waveforms to the vestibular system and/or the nervous system of a patient prior to, currently with and/or after administration of one or more active agents and/or therapies.

"Chronic treatment," "Chronically treating," or the like refers to a therapeutic treatment carried out at least 2 to 3 times a week (or in some embodiments at least daily) over an extended period of time (typically at least one to two weeks, and in some embodiments at least one to two months), for as long as required to achieve and/or maintain therapeutic efficacy for the particular condition or disorder for which the treatment is carried out.

"Waveform" or "waveform stimulus" as used herein refers to the thermal stimulus (heating, cooling) delivered to the ear canal of a subject through a suitable apparatus to carry out the methods described herein. "Waveform" is not to be confused with "frequency," the latter term concerning the rate of delivery of a particular waveform. The term "waveform" is used herein to refer to one complete cycle thereof, unless additional cycles (of the same, or different, waveform) are indicated. As discussed further below, time-varying waveforms may be preferred over constant temperature applications in carrying out the present invention.

"Actively controlled waveform" or "actively controlled time-varying waveform" as used herein refers to a waveform stimulus in which the intensity of the stimulus or temperature of the earpiece delivering that stimulus, is repeatedly adjusted, or substantially continuously adjusted or driven, throughout the treatment session, typically by control circuitry or a controller in response to active feedback from a suitably situated temperature sensor (e.g., a temperature sensor mounted on the earpiece being driven by a thermoelectric device), so that drift of the thermal stimulus from that which is intended for delivery which would otherwise occur due to patient contact is minimized.

In general, a waveform stimulus used to carry out the present invention comprises a leading edge, a peak, and a trailing edge. If a first waveform stimulus is followed by a second waveform stimulus, then the minimal stimulus point therebetween is referred to as a trough.

The first waveform of a treatment session is initiated at a start point, which start point may be the at or about the subject's body temperature at the time the treatment session is initiated (typically a range of about 34 to 38 degrees Centigrade, around a normal body temperature of about 37 degrees Centigrade. The lower point, 34, is due to the coolness of the ear canal. It typically will not be above about 37 unless the patient is febrile). Note that, while the subject's ear canal may be slightly less than body temperature (e.g., about 34 to 36 degrees Centigrade), the starting temperature for the waveform is typically body temperature (the temp of the inner ear), or about 37 degrees Centigrade. In some embodiments, however, the temperature of the treatment device may not have equilibrated with the ear canal prior to the start of the treatment session, and in such case the start point for at least the first waveform stimulus may be at a value closer to room temperature (about 23 to 26 degrees Centigrade).

The waveform leading edge is preferably ramped or time-varying: that is, the amplitude of the waveform increases through a plurality of different temperature points over time (e.g., at least 5, 10, or 15 or more distinct temperature points, and in some embodiments at least 50, 100, or 150 or more distinct temperature points, from start to peak). The shape of the leading edge may be a linear ramp, a curved ramp (e.g., convex or concave; logarithmic or exponential), or a combination thereof.

Subjects may be treated with the present invention for any reason. In some embodiments, disorders for which treatment may be carried out include, include, but are not limited to, migraine headaches (acute and chronic), depression, anxiety (e.g. as experienced in post-traumatic stress disorder ("PTSD") or other anxiety disorders), spatial neglect, Parkinson's disease, seizures (e.g., epileptic seizures), diabetes (e.g., type II diabetes), etc.

Headaches that may be treated by the methods and apparatuses of the present invention include, but are not limited to, primary headaches (e.g., migraine headaches, tension-type headaches, trigeminal autonomic cephalagias and other primary headaches, such as cough headaches and exertional headaches) and secondary headaches. See, e.g., International Headache Society Classification ICHD-II.

Migraine headaches that may be treated by the methods and apparatuses of the present invention may be acute/chronic and unilateral/bilateral. The migraine headache may be of any type, including, but not limited to, migraine with aura, migraine without aura, hemiplegic migraine, opthalmoplegic migraine, retinal migraine, basilar artery migraine, abdominal migraine, vestibular migraine and probable migraine. As used herein, the term "vestibular migraine" refers to migraine with associated vestibular symptoms, including, but not limited to, head motion intolerance, unsteadiness, dizziness and vertigo. Vestibular migraine includes, but is not limited to, those conditions sometimes referred to as vertigo with migraine, migraine-associated dizziness, migraine-related vestibulopathy, migrainous vertigo and migraine-related vertigo. See, e.g., Teggi et al., HEADACHE 49:435-444 (2009).

Tension-type headaches that may be treated by the methods and apparatuses of the present invention, include, but are not limited to, infrequent episodic tension-type headaches, frequent episodic tension-type headaches, chronic tension-type headache and probable tension-type headache.

Trigeminal autonomic cephalagias that may be treated by the methods and apparatuses of the present invention, include, but are not limited to, cluster headaches, paroxysmal hemicranias, short-lasting unilateral neuralgiform headache attacks with conjunctival injection and tearing and probable trigeminal autonomic cephalagias. Cluster headache, sometimes referred to as "suicide headache," is considered different from migraine headache. Cluster headache is a neurological disease that involves, as its most prominent feature, an immense degree of pain. "Cluster" refers to the tendency of these headaches to occur periodically, with active periods interrupted by spontaneous remissions. The cause of the disease is currently unknown. Cluster headaches affect approximately 0.1% of the population, and men are more commonly affected than women (in contrast to migraine headache, where women are more commonly affected than men).

Other primary headaches that may be treated by the methods and apparatuses of the present invention, include, but are not limited to, primary cough headache, primary exertional headache, primary headache associated with sexual activity, hypnic headache, primary thunderclap headache, hemicranias continua and new daily-persistent headache.

Additional disorders and conditions that can be treated by the methods and systems of the present invention include, but are not limited to, neuropathic pain (e.g., migraine headaches), tinnitus, brain injury (acute brain injury, excitotoxic brain injury, traumatic brain injury, etc.), spinal cord injury, body image or integrity disorders (e.g., spatial neglect), visual intrusive imagery, neuropsychiatric disorders (e.g. depression), bipolar disorder, neurodegenerative disorders (e.g. Parkinson's disease), asthma, dementia, insomnia, stroke, cellular ischemia, metabolic disorders, (e.g., diabetes), post-traumatic stress disorder ("PTSD"), addictive disorders, sensory disorders, motor disorders, and cognitive disorders.

Sensory disorders that may be treated by the methods and apparatuses of the present invention include, but are not limited to, vertigo, dizziness, seasickness, travel sickness cybersickness, sensory processing disorder, hyperacusis, fibromyalgia, neuropathic pain (including, but not limited to, complex regional pain syndrome, phantom limb pain, thalamic pain syndrome, craniofacial pain, cranial neuropathy, autonomic neuropathy, and peripheral neuropathy (including, but not limited to, entrapment-, heredity-, acute inflammatory-, diabetes-, alcoholism-, industrial toxin-, Leprosy-, Epstein Barr Virus-, liver disease-, ischemia-, and drug-induced neuropathy)), numbness, hemianesthesia, and nerve/root plexus disorders (including, but not limited to, traumatic radiculopathies, neoplastic radiculopathies, vaculitis, and radiation plexopathy).

Motor disorders that may be treated by the method and apparatuses of the present invention include, but are not limited to, upper motor neuron disorders such as spastic paraplegia, lower motor neuron disorders such as spinal muscular atrophy and bulbar palsy, combined upper and lower motor neuron syndromes such as familial amyotrophic lateral sclerosis and primary lateral sclerosis, and movement disorders (including, but not limited to, Parkinson's disease, tremor, dystonia, Tourette Syndrome, myoclonus, chorea, nystagmus, spasticity, agraphia, dysgraphia, alien limb syndrome, and drug-induced movement disorders).

Cognitive disorders that may be treated by the method and apparatuses of the present invention include, but are not limited to, schizophrenia, addiction, anxiety disorders, depression, bipolar disorder, dementia, insomnia, narcolepsy, autism, Alzheimer's disease, anomia, aphasia, dysphasia, parosmia, spatial neglect, attention deficit hyperactivity disorder, obsessive compulsive disorder, eating disorders, body image disorders, body integrity disorders, post-traumatic stress disorder, intrusive imagery disorders, and mutism.

Metabolic disorders that may be treated by the present invention include diabetes (particularly type II diabetes), hypertension, obesity, etc.

Addiction, addictive disorders, or addictive behavior that may be treated by the present invention includes, but is not limited to, alcohol addiction, tobacco or nicotine addiction (e.g., using the present invention as a smoking cessation aid), drug addictions (e.g., opiates, oxycontin, amphetamines, etc.), food addictions (compulsive eating disorders), etc.

In some embodiments, the subject has two or more of the above conditions, and both conditions are treated concurrently with the methods and systems of the invention. For example, a subject with both depression and anxiety (e.g., PTSD) can be treated for both, concurrently, with the methods and systems of the present invention.

The methods and systems according to embodiments of the present invention utilize thermoelectric devices (TEDs) to induce physiological and/or psychological responses in a subject for medically diagnostic and/or therapeutic purposes. Subjects to be treated and/or stimulated with the methods, devices and systems of the present invention include both human subjects and animal subjects. In particular, embodiments of the present invention may be used to diagnose and/or treat mammalian subjects such as cats, dogs, monkeys, etc. for medical research or veterinary purposes.

As noted above, embodiments according to the present invention utilize TEDs to provide an in-ear stimulator for administering thermal stimulation in the ear canal of the subject. The ear canal serves as a useful conduit to the individual's vestibular system and to the vestibulocochlear nerve. Without wishing to be bound by any particular theory, it is believed that thermal stimulation of the vestibular system is translated into electrical stimulation within the central nervous system ("CNS") and propagated throughout the brain, including but not limited to the brain stem, resulting in certain physiological changes that may be useful in treating various disease states (increased blood flow, generation of neurotransmitters, etc). See, e.g., Zhang, et al. *Chinese Medical J.* 121:12:1120 (2008) (demonstrating increased ascorbic acid concentration in response to cold water CVS).

As illustrated in FIG. 1 an in-ear stimulation system 10 includes an in-ear stimulation device 100 and a controller or base 500. The base 500 includes a housing 510 and power cord 560. The in-ear stimulation device 100 includes an earcup 200 with connectors 320 and a headband 400. The base connectors or power cords 560 and the connectors 320 are configured for connecting to circuitry within the earcups 200. For example, the power cord 560 may provide power from the base 500 to the earcups 200, and the connectors 320 may communicate operational instructions from a processor in the base 500 or send data to a processor in the base 500. The base 500 can have a separate power cord (not shown) to receive power from a power source, such as a standard wall outlet. As described in more detail in FIGS. 3-6, the in-ear stimulation device 100 includes earpieces 230 that are configured to deliver a thermal stimulation to the ear canal and vestibular system of a user.

Figure 2:
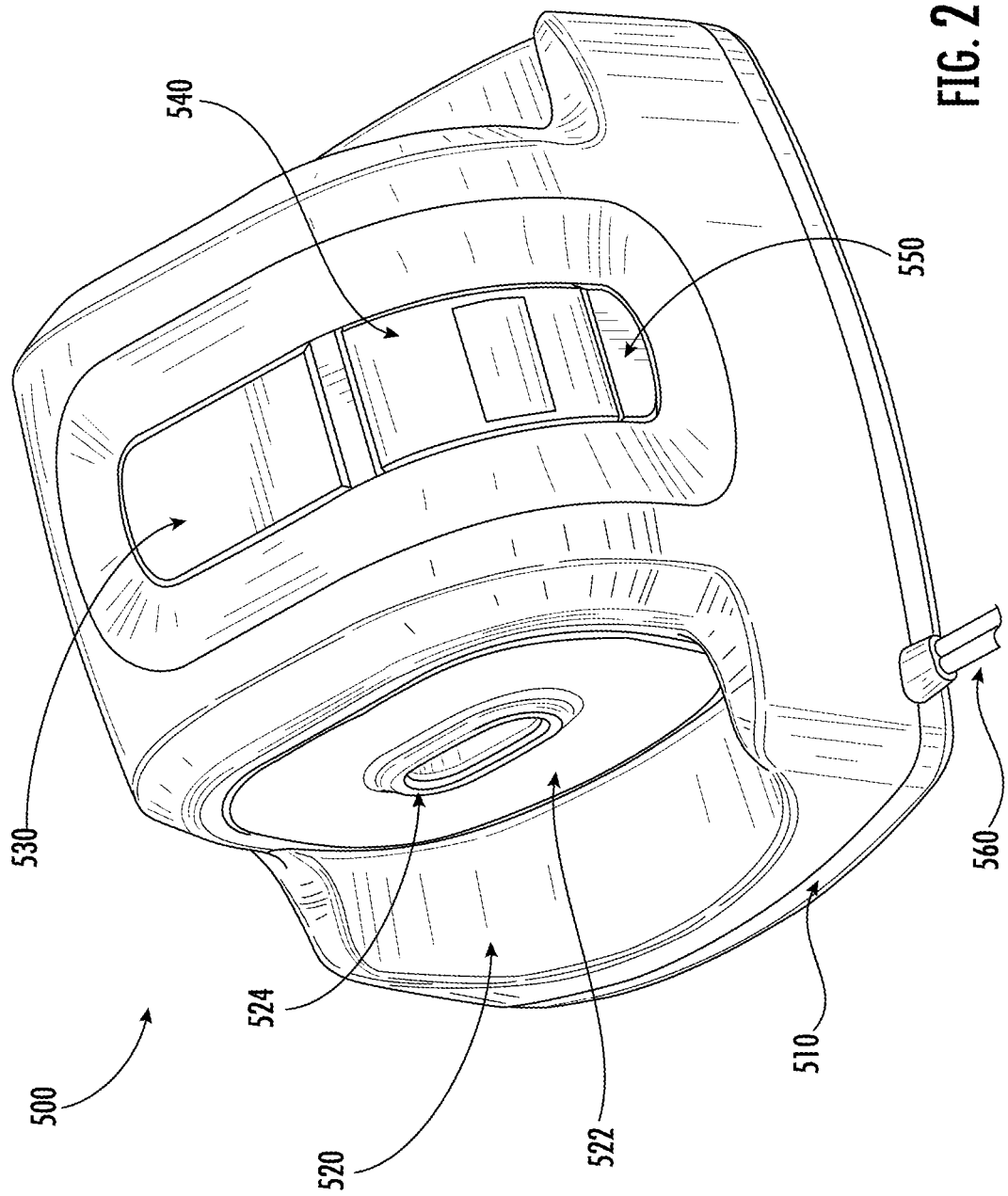
FIG. 2 is perspective view of the controller base of the in-ear stimulation system FIG. 1.

As shown in FIG. 2, the base 500 includes two earcup holders 520 with a pad 522 and an earpiece holder 524 for holding the earcups 200. The housing 510 can include control circuitry for communicating with and controlling the in-ear stimulation device 100. The housing 510 further includes an input reader, such as a barcode scanner 530, a user interface, such as a display 540, and a start/stop momentary switch 550. The base 500 may include a separate power switch, for example, on the back of the base 500, for turning power to the base 500 on or off.

In some embodiments, the circuitry of the controller base 500 is configured to receive and/or store instructions for providing thermal waveforms and other instructions for treatment protocols, such as a treatment "prescription." Treatment prescriptions are described in U.S. Pat. No. 9,526,653, issued Dec. 27, 2016. For example, a barcode that is associated with a treatment prescription in a database or lookup table stored in the memory of the controller base 500 may be read by the barcode scanner 530, and the display 540, which may be a touch screen display, may be used as a user interface and/or to display instructions to the user based on the treatment prescription identified by the barcode scanner 530. The circuitry of the controller base 500 may include libraries of treatment protocols and other instructions for operating the in-ear stimulation device. In some embodiments, the treatment protocols are associated with barcodes. Moreover, the libraries of treatment protocols stored by the controller base 500 may be loaded into a memory by a connection to an outside computer system such that treatment protocols may be designed by a physician or other prescriber. However, it should be understood that the barcode scanner 530 and display 540 may further be used to load a particular treatment session from a set of treatment sessions and/or to record compliance with the treatment protocols.

Figure 3:
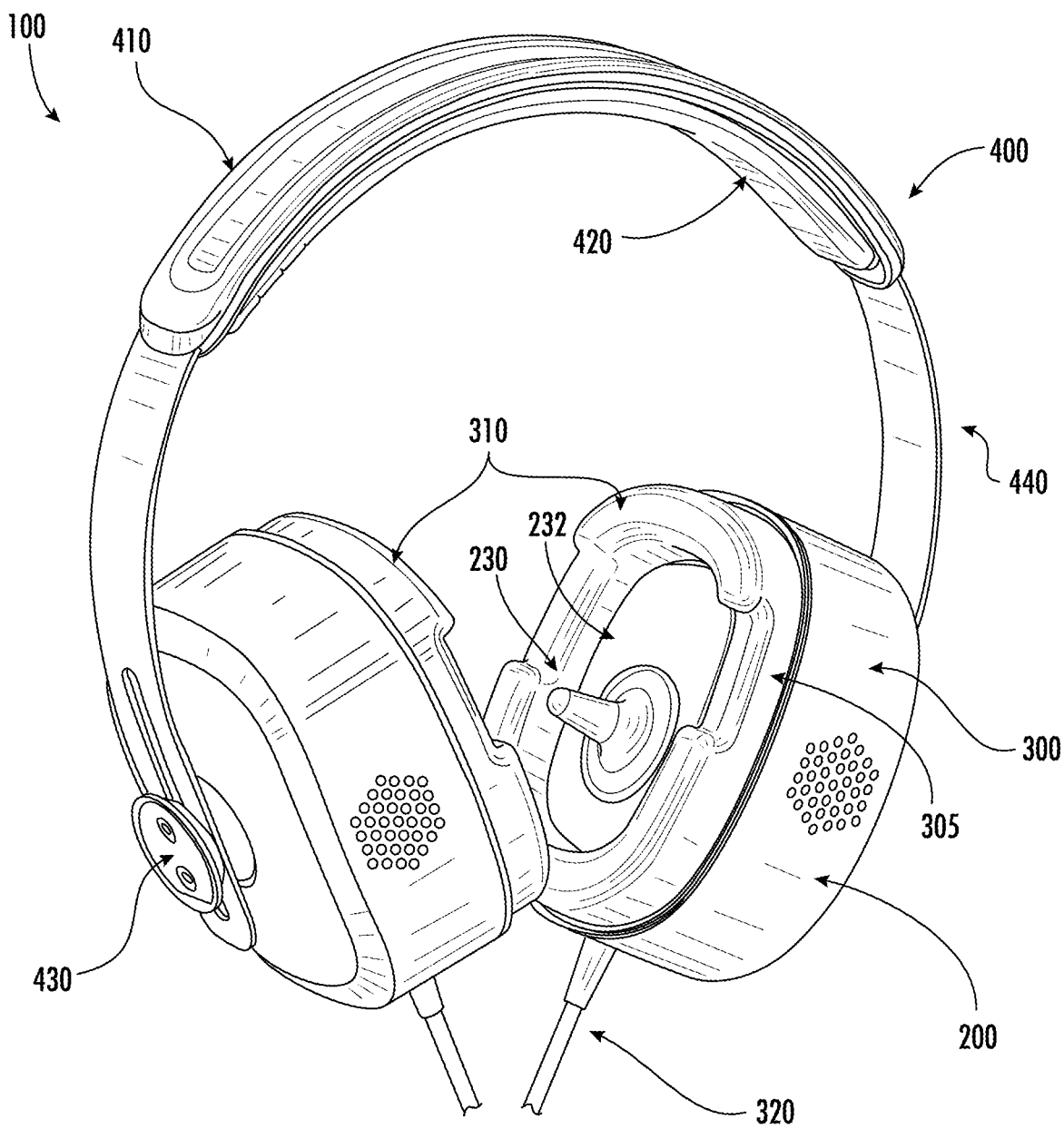
FIG. 3 is perspective view of the headset of the in-ear stimulation system of FIG. 1.
Figure 4:
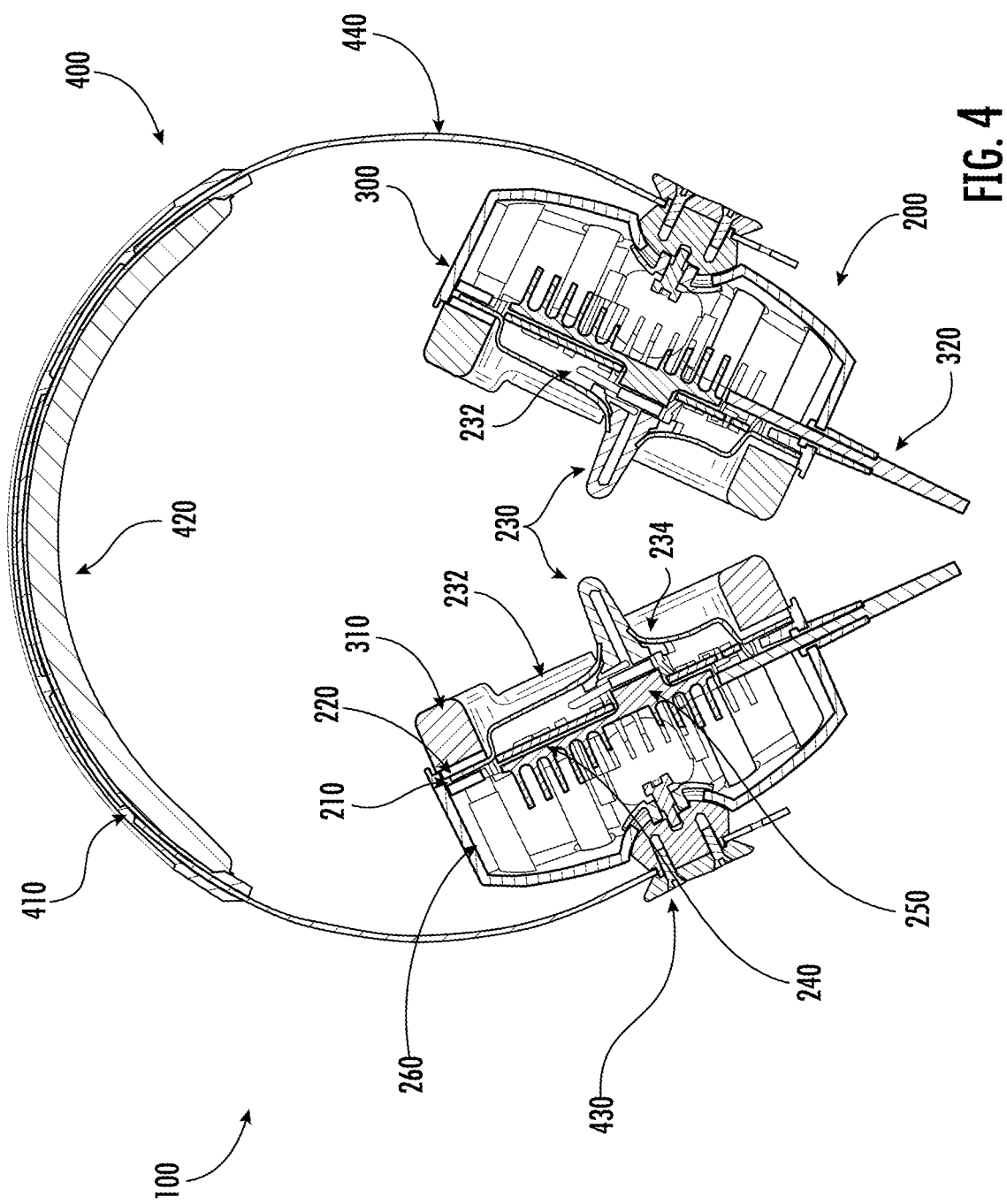
FIG. 4 is a cross sectional view of the headset of FIG. 1.

The treatment protocols and other control instructions from the controller base 500 may be used to control the in-ear stimulation device 100. Referring to FIGS. 3 and 4, the in-ear stimulation device 100 includes earcups 200 having a housing 300 for holding the earpieces 230 in the ear canals of a user, cushioning members or foam padding 310, and connectors 320. The outer portion of the foam padding 310 has a recess 305 that is configured to receive, for example, eyewear, when the earcups 200 are positioned on the ears of the user to increase comfort to the user while maintaining the position of the earcups 200.

The earcups 200 include a frame 210 within the housing 300 (FIG. 4). The frame 210 holds a flexible inner diaphragm or tensioning member 220 that is used to hold the earpiece 230. The earpiece 230 is fixed with respect to a substrate or circuit board 240 and heat sink 250 in the housing 300. In particular, the circuit board 240 is adhered to the heat sink 250, and the earpiece 230 is mounted to heatsink 250, and the tensioning member 220 is connected to the circuit board 240. In addition, optional fans 260 are mounted on a side of the frame 210 to provide further heat dissipation from the heatsink 250. As illustrated, the earpiece 230 is connected to an outer flexible diaphragm 232. The outer diaphragm 232 protects the circuit components of the circuit board 240 from environmental contamination and has an aperture into which the earpiece 230 fits. In some embodiments, the earpiece 230 may include a groove into which the outer diaphragm 232 fits. The headband 400 includes an overmold portion 410 and a gimbal 430 or other rotatable support on an arc 440. The overmold portion 410 may provide a mating partner to the headband pad 420, which is attached to the arc 440 by a hook and loop or other fastener or adhesive. The headband arc 440 may be formed of steel or other suitably strong material. The gimbal 430 provides adjustment of the length of the headband arc 440 by sliding along the channel in the headband arc 440 and adjustable placement of the earcups 430 for comfort and adjusting for the head size of the wearer.

In this configuration, the controller base 500 can communicate and provide instructions for controlling the circuit board 240 to provide a thermal waveform to the earpiece 230. Example waveforms and treatments, including chronic treatment, acute treatment, and adjuvant treatment of various conditions by providing time varying waveforms to the ear canal of the user for vestibular simulation may be found, for example, in U.S. Pat. No. 9,532,900, issued Jan. 3, 2017.

Figure 5A:
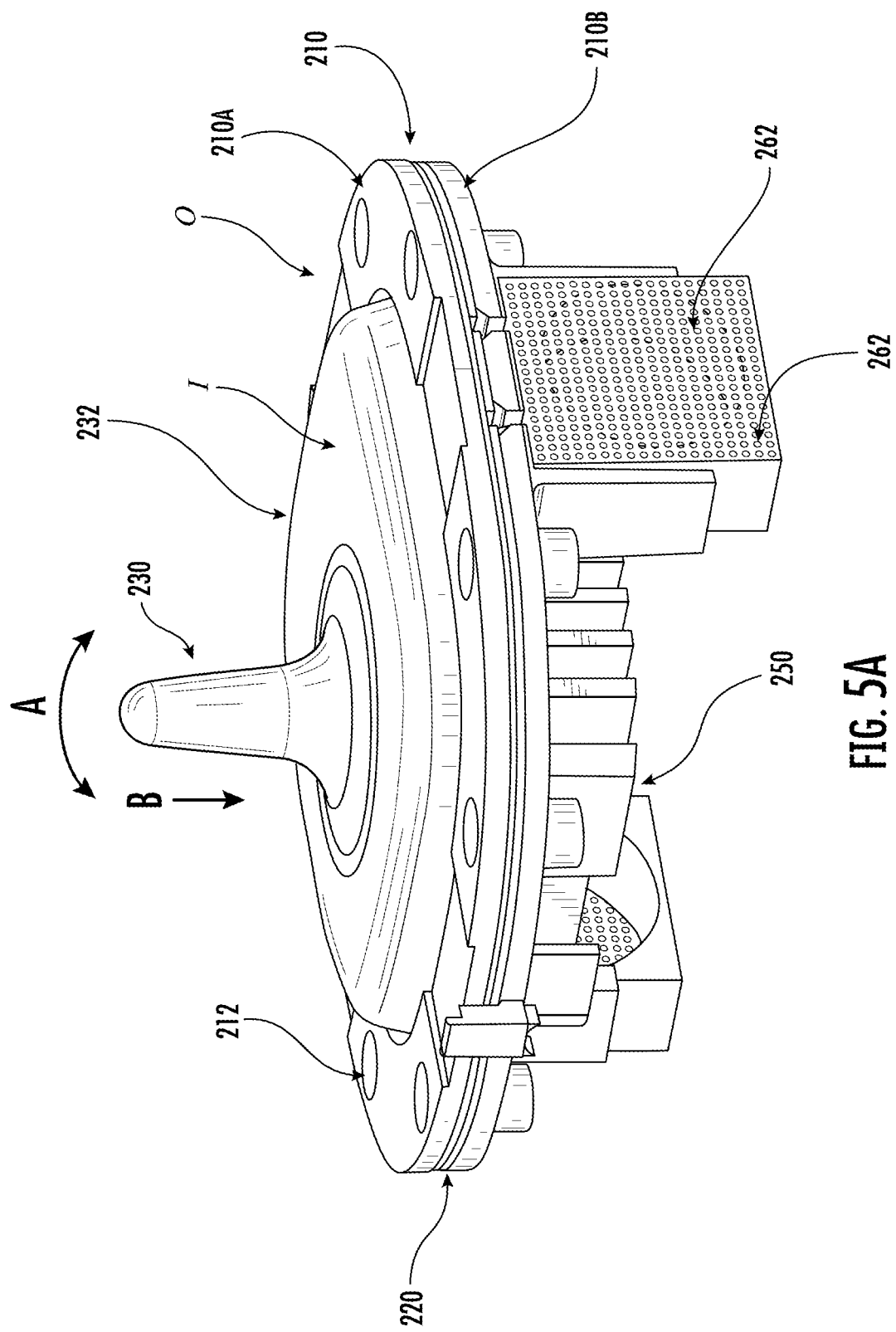
FIG. 5A-5C are side perspective views of an in-ear stimulation device in the headset of FIG. 1.
Figure 5B:
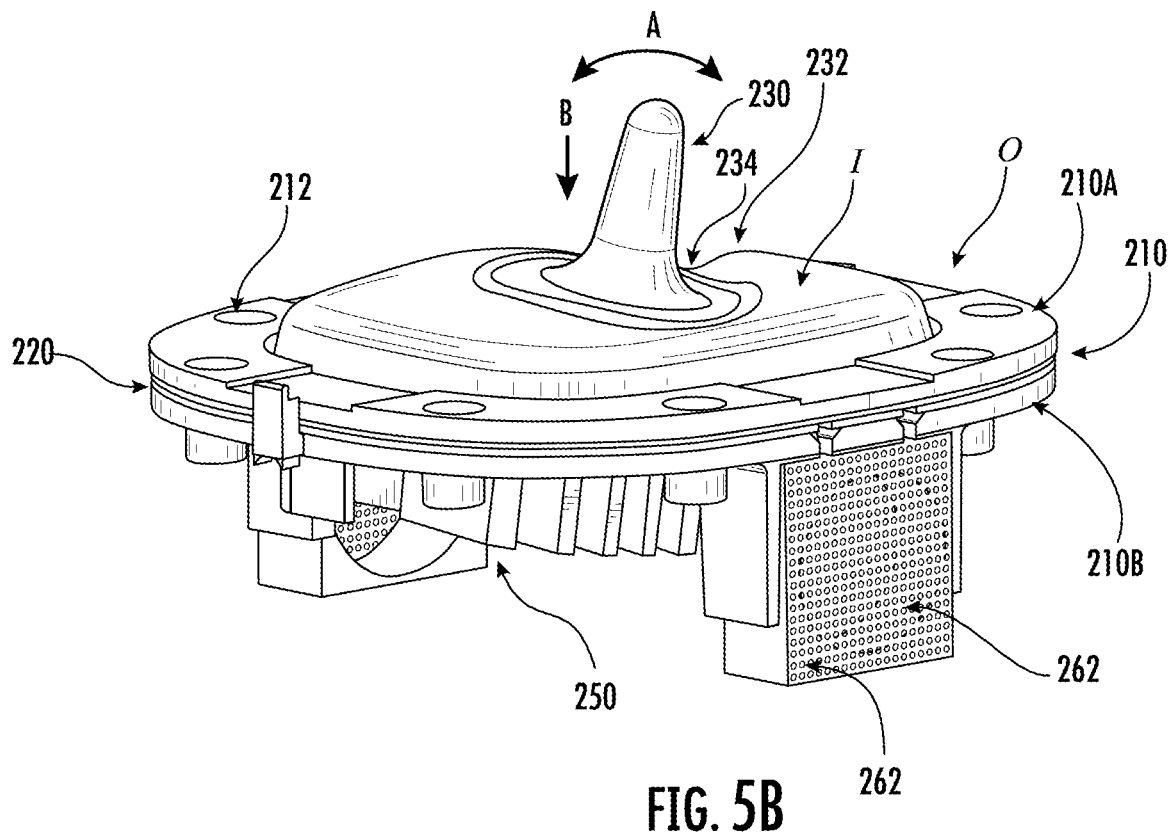
Figure 5C:
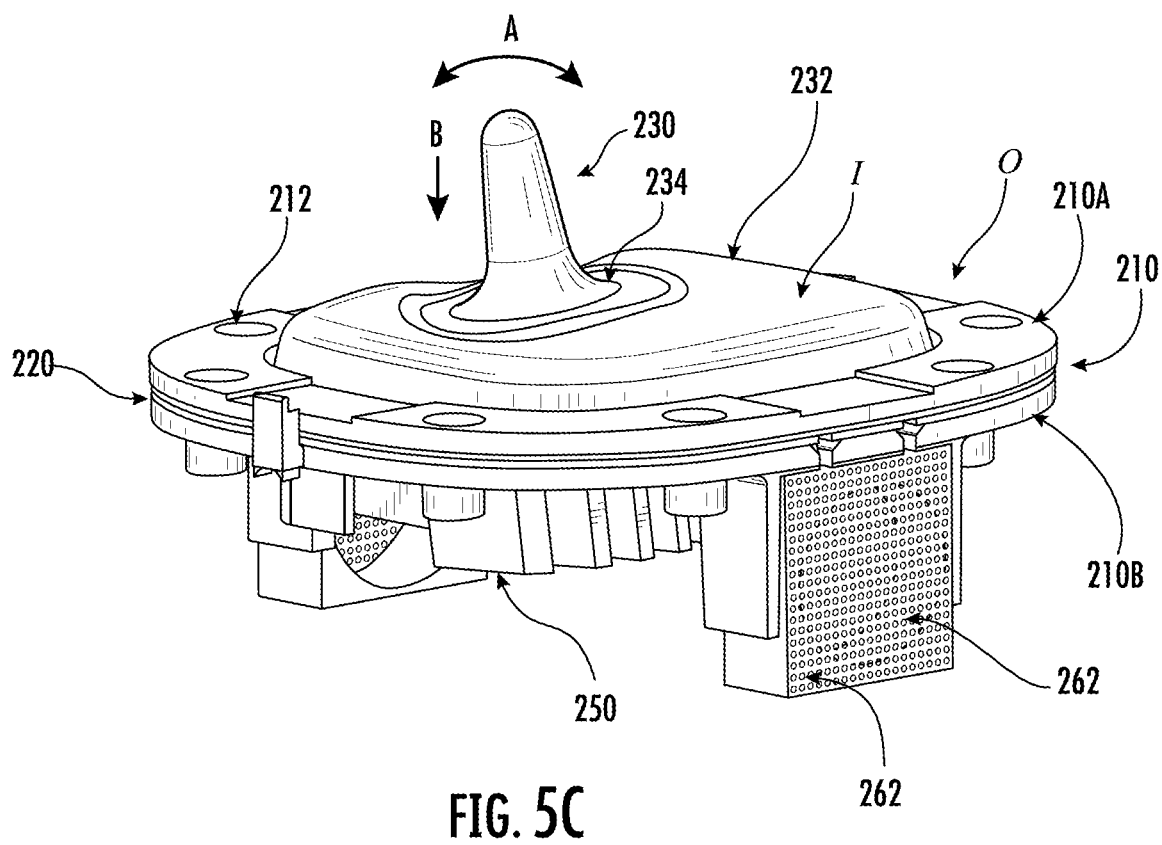

In addition, the flexible tensioning member 220 may allow the earpiece 230 to tilt with respect to the earcup housing 300 to provide additional comfort to the user while maintaining a snug fit in the ear canal to enhance thermal conductivity within the ear canal. As shown in FIG. 5, the frame 210 includes a top frame member 210A and a bottom frame member 210B. The frame members 210A, 210B are joined by fasteners 212 with the tensioning member 220 held between the frame members 210A, 210B. The frame 210 defines an inner portion I and an outer perimeter O. The earpiece 230, the circuit board 240, and the heat sink 250 are held in position in the inner portion I by the tensioning member 220.

When the earpiece 230 is positioned on the user and enters the ear canal, the tensioning member 220 permits tilt of the earpiece 230 along the arrow A with respect to the frame 210 and the earcups 200. Accordingly, the angle of the earpiece 230 with respect to the earcups 200 may be automatically adjusted by the anatomy of the user's ear and ear canal for increased comfort. In addition, the earpiece 230 may further move in the direction of arrow B during and after insertion of the earpiece into the ear canal to decrease pressure exerted by the earpiece within the ear canal. In some embodiments, the user may experience increased comfort due to the automatic adjustments of the earpieces 230 within the earcups 200, which may result in increased compliance with treatment protocols and user acceptance.

As illustrated in FIGS. 6A-6B, the tensioning member 220 may be a flexible and/or planar elastomeric sheet that permits tilting of the earpiece 230 within the frame 210. The material of the elastic sheet of the tensioning member 220 may be silicone and/or may have a durometer (shore) value of 30-40. The earpiece 230 includes thermoelectric devices 236 for heating and cooling the earpiece 230, which are connected to the heat sink 250. As shown in FIGS. 5 and 6A-6B, the earpiece 230, together with the flexible diaphragm 232, connector 234, circuit board 240 and heat sink 250 may move and tilt sideways in the direction of arrow A. That is, in some embodiments, the earpiece 230, thermoelectric device 236, and heat sink 250 are suspended on the tensioning member 220.

Thus, the tensioning member 220 may permit the earpiece 230 to move with respect to the housing 300 in the directions of arrows A and B. Thus, the tensioning member 220 exerts a force towards the ear canal of the user while also allowing movement of the earpiece in the directions of arrows A and B. The angle of insertion, e.g., the angle at which the earpiece 230 enters the ear canal of the wearer, may be adjusted automatically as the earcup 200 is positioned on the user's head and ear. That is, as the earpiece 230 enters the ear canal of the user, the ear canal and shape of the user's ear may cause the earpiece 230 to bend in a direction that is in line with the user's ear canal shape and angle with respect to placement of the earcups 200. The diaphragm 232, which protects the electrical components of the circuit board 240, may include an aperture for receiving the earpiece 230 and may further extend over the tensioning member 220. In some embodiments, the diaphragm 232 is formed of the same elastomeric material as the tensioning member 220.

As shown in FIGS. 7A-7C, in some embodiments, the elastomeric member 220 includes at least one fold 222 adjacent the circuit board 240. The folds 222 allow for increased tilting and movement of the circuit board 240 along the arrows A and B (FIGS. during insertion of the earpiece 230 into the ear canal of the user.

The cushioning member 310 may be used to balance or counteract the inward force of the headband on the earpiece 230 for additional comfort and to reduce or prevent potentially painful pressure on the ear canal from the earpiece 230. For example, if the cushioning member 310 were removed, pressure from the headband 400 may overwhelm and be greater than the ability of the tensioning member 220 to balance the inward pressure in the ear canal. In some embodiments, the cushioning member 310 may be removable or the user may select a cushioning member from a set of cushioning members that have different thicknesses. FIGS. 8A-8C are perspective views of a small cushioning member (FIG. 8A), a medium cushioning member (FIG. 8B), and a large cushioning member (FIG. 8C).

As illustrated, the earpiece 230 is connected to the tensioning member 220 by the circuit board 240 and connector 234. As shown in FIG. 6B, the circuit board 240 is connected to thermoelectric devices 236, which are mounted on the hear sink 250 and earpiece 230 via thermally conductive pads 230A. However, thermal grease or conductive epoxy may also be used. The earpiece 230 includes a shaft 230B, which may be used, for example, to provide a passageway for receiving a temperature sensor.

Although the earpiece 230 is connected to the tensioning member 220 by the circuit board 240, it should be understood that the earpiece 230 could be connected to the tensioning member 220 directly or via other intervening components to permit flexible tilting and movement of the earpiece 230 within the frame 210 and/or earcup 200, although the earpiece 230, thermoelectric device 236, and heat sink 250 are typically thermally connected to one another in a thermal stack that is suspended in a single unit by the tensioning member 220.

In some embodiments, the slew rate for the earpieces 230 is about 15° C./minute or greater for cooling the earpiece 230 and 20° C./minute or greater for heating the earpiece 230. Heating the earpiece may be faster and more efficient than cooling; however, slew rates that are 20° C./minute or greater may increase side effects, such as motion sickness, depending on the individual tolerance of the user. The earpiece 230 may be formed of any suitable thermoconductive material, such as aluminum. In some embodiments, such as when an fMRI or other imaging is performed during use, ceramic or other materials may be used to reduce magnetic field distortion associated with aluminum. In some embodiments, the aluminum is anodized.

Thin film TEDs, Peltier coolers/heaters or transducers may be used as thermoelectric devices 236 to heat or cool the earpiece 230 in some embodiments, including, but not limited to, the thin film TEDs described in U.S. Pat. No. 6,300,150 and U.S. Patent Publication Nos. 2007/0028956 and 2006/0086118; however, any suitable TED, such as semiconductor diode TED's, may be used. The thermoelectric devices 236 may be controlled by control circuitry in the controller base 500, for example, using temperature feedback. Such TEDs may also incorporate a temperature sensing function, so that temperature sensing can be accomplished through the same device without the need for a separate temperature sensor. In some embodiments, a separate temperature sensor may be used, such as a thermistor or other temperature sensing element that is positioned in the earpiece 230 and used as a feedback sensor to allow the circuitry in the base 500 to maintain the proper temperature for a given thermal waveform. TEDs are commercially available from TE Technology, Inc, (Traverse City, MI, USA), Nextreme Thermal Solultions (Durham, NC, USA) (e.g., OptoCooler™ Series (UPT40 and UPF4), Eteg™ UPF40), Micropelt, GmbH (Freiburg, Germany)(e.g., MPC-D303 and MPC-D305), and Phononic (Durham, NC, USA). Although embodiments according to the invention are described herein with respect to TEDs, it should be understood that any suitable type of thermal device may be used, including optical heating (e.g., using a laser) and ultrasound heating (e.g., a piezoelectric heating device). However, TEDs may be preferred because TEDs allow for both heating and cooling to increase the precision of actively controlled, time varying caloric vestibular stimulation. TEDs may be provided that include a heat flux of 80-120 W/cm$^2$ or more. The TEDs may be generally rectangular in shape, with typical rectangular areas being about 2×1 mm or 5×2 mm or more and having a height profile of 1 mm or 0.65 mm or 0.5 mm or less. In particular embodiments, the TED is about a rectangular shape having sides of about 12-13 mm and a height profile of about 3 mm. When more than one TED is used, the TEDs may be connected in parallel or in series to provide thermal changes to a desired region of an earpiece and/or heat sink.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. An in-ear stimulation device for administering caloric stimulation to the ear canal of a subject, comprising:
   a frame defining a perimeter and a center region;
   at least one tensioning member in the center region of the frame and being held by the frame;
   an earpiece connected to the tensioning member in the center region of the frame, wherein the frame is configured to generally rest on a head and around an ear of the subject such that the earpiece is positioned in the ear canal of the subject and the tensioning member positions the earpiece in the ear canal of the subject,
   wherein the tensioning member comprises a planar sheet that extends from the center region adjacent the earpiece towards the perimeter of the frame.

2. The in-ear stimulation device of claim 1, wherein the tensioning member is flexible such that the tensioning member is configured to flex thereby reduce a force on the earpiece in the ear canal.

3. The in-ear stimulation device of claim 2, wherein the tensioning member is secured by the frame so that the tensioning member is taut so as to achieve a thermally conductive fit in use between the earpiece and the ear canal of the subject.

4. The in-ear stimulation device of claim 2, further comprising a heat sink rigidly coupled to the earpiece and configured to move together with the earpiece when the tensioning member flexes.

5. The in-ear stimulation device of claim 1, further comprising a thermoelectric device thermally coupled to the earpiece.

6. The in-ear stimulation device of claim 5, further comprising a heat sink coupled to the thermoelectric device on a side thereof that is opposite the earpiece.

7. The in-ear stimulation device of claim 1, wherein the earpiece comprises a generally cylindrical portion having a domed distal end that is configured to be positioned in the ear canal of the subject.

8. The in-ear stimulation device of claim 1, wherein the earpiece is thermally conductive.

9. The in-ear stimulation device of claim 1, further comprising a cushioning member on the frame and configured to rest on the head and around the ear of the subject.

10. The in-ear stimulation device of claim 9, wherein the cushioning member is removable whereby the cushioning member is configured to be selected by a user from a set of cushioning members of different sizes.

11. The in-ear stimulation device of claim 9, wherein the cushioning member comprises a recess on opposing sides thereof, the recess being sized and configured to allow eyewear in use on the user to be within the recess.

12. The in-ear stimulation device of claim 1, further comprising a headband configured to hold the frame in position on the subject.

13. The in-ear stimulation device of claim 1, wherein the tensioning member comprises an elastic sheet.

14. An in-ear stimulation device for administering caloric stimulation to the ear canal of a subject, comprising:
- a frame defining a perimeter and having a center region;
- at least one tensioning member in the center region of the frame and being held by the frame;
- an earpiece connected to the tensioning member in the center region of the frame;
- a headband configured to position the frame adjacent the head and around an ear of the subject such that the earpiece is positioned in the ear canal of the subject and the tensioning member positions the earpiece in the ear canal of the subject;
- wherein the tensioning member comprises a planar sheet that extends from the center region adjacent the earpiece towards the perimeter of the frame.

15. The in-ear stimulation device of claim 14, wherein the tensioning member is flexible such that the tensioning member is configured to flex thereby reduce a force on the earpiece in the ear canal.

16. The in-ear stimulation device of claim 15, wherein the tensioning member is secured by the frame so that the member is sufficiently taut so as to achieve a thermally conductive fit in use between the earpiece and the ear canal of the subject.

17. The in-ear stimulation device of claim 15, further comprising a heat sink rigidly coupled to the earpiece and configured to move together with the earpiece when the tensioning member flexes.

18. The in-ear stimulation device of claim 14, wherein the frame is spaced apart from the head of the subject.

19. The in-ear stimulation device of claim 14, further comprising a substrate having the earpiece mounted thereon, wherein the at least one tensioning member connects the frame to the substrate.

20. The in-ear stimulation device of claim 14, further comprising a cushioning member on the frame and configured to rest on the head and around the ear of the subject.

21. The in-ear stimulation device of claim 20, wherein the cushioning member is removable whereby the cushioning member is configured to be selected by a user from a set of cushioning members of different sizes.

22. The in-ear stimulation device of claim 20, wherein the cushioning member comprises a recess on opposing sides thereof, the recess being sized and configured to allow eyewear in use on the user to be within the recess.

* * * * *